United States Patent
Van Herk

(10) Patent No.: US 8,145,318 B2
(45) Date of Patent: Mar. 27, 2012

(54) MEASUREMENT AND STIMULATION OF MUSCLE TISSUE

(75) Inventor: Johannes Johanna Van Herk, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 914 days.

(21) Appl. No.: 11/997,783

(22) PCT Filed: Jul. 20, 2006

(86) PCT No.: PCT/IB2006/052484
§ 371 (c)(1),
(2), (4) Date: Jul. 9, 2008

(87) PCT Pub. No.: WO2007/017778
PCT Pub. Date: Feb. 15, 2007

(65) Prior Publication Data
US 2009/0118790 A1    May 7, 2009

Related U.S. Application Data

(60) Provisional application No. 60/706,122, filed on Aug. 5, 2005.

(30) Foreign Application Priority Data
Dec. 20, 2005 (EP) .................................. 05112457

(51) Int. Cl.
*A61N 1/36* (2006.01)
(52) U.S. Cl. ........................................................ 607/48
(58) Field of Classification Search .................. None
See application file for complete search history.

(56) References Cited

U.S. PATENT DOCUMENTS

| 4,612,934 | A | * | 9/1986 | Borkan ........................... 607/62 |
| 5,048,522 | A |   | 9/1991 | Petrofsky |
| 5,324,322 | A | * | 6/1994 | Grill et al. ..................... 607/118 |
| 5,702,428 | A | * | 12/1997 | Tippey et al. ................... 607/41 |
| 5,904,712 | A | * | 5/1999 | Axelgaard ..................... 607/148 |
| 6,301,500 | B1 | * | 10/2001 | Van Herk et al. ............... 607/2 |
| 2004/0034396 | A1 |   | 2/2004 | Freed et al. |
| 2004/0158298 | A1 | * | 8/2004 | Gliner et al. .................... 607/48 |
| 2006/0085049 | A1 | * | 4/2006 | Cory et al. ...................... 607/48 |
| 2006/0190057 | A1 | * | 8/2006 | Reese ............................... 607/46 |

FOREIGN PATENT DOCUMENTS

| EP | 0938911 A2 | 9/1999 |
| JP | 5337203 A | 12/1993 |
| JP | 2001025510 A | 1/2001 |
| WO | 2004050172 A1 | 6/2004 |
| WO | 2004087258 A1 | 10/2004 |

* cited by examiner

*Primary Examiner* — Kennedy Schaetzle

(57) ABSTRACT

An apparatus (1) for electrical stimulation of muscle tissue. The apparatus has an electrode system (10) with an electrode array (13). The array has a plurality of electrode pads (12) and can be placed in electrical contact with the muscle tissue. The electrode system Further has a sensor (30; 31-36) for sensing a property of the muscle tissue. The property forms a measure for the activity of the muscle tissue. The apparatus (1) has an electrode selector (530) for selecting one or more stimulating electrode pads. A signal generator (531) is connected to the electrode array (13) for providing an electrical stimulation signal to the stimulation electrode pad. A signal processor (532) is connected to said sensor (30; 31-36), for determining from the sensor signal a value of the muscle activity and outputting the value in a for humans perceptible form. This reduces the accuracy required to position the electrode system (10) and increases the accuracy of measuring the muscle tissue activity.

16 Claims, 5 Drawing Sheets

US 8,145,318 B2

MEASUREMENT AND STIMULATION OF MUSCLE TISSUE

FIELD OF THE INVENTION

The invention relates to an apparatus for electrical stimulation of muscle tissue. The invention also relates to an operation device for such an apparatus. The invention further relates to an electrode for an apparatus for electrical stimulation of muscle tissue and to a method for stimulating muscle tissue.

BACKGROUND OF THE INVENTION

From European patent publication EP 938 911 A2, an apparatus for medical treatment is known. The apparatus is operatively coupled to an electrode adapted to be contacted to a body portion or inserted into a body cavity. The apparatus has an EMG signal processor for performing a signal processing related to an EMG signal and a display unit for displaying information related to a medical treatment based on the EMG signal. The apparatus further has a stimulation signal generator for generating a stimulation signal and proving the stimulation signal to the electrode However, a disadvantage of the apparatus known from this prior art document is that the electrode has to be positioned accurately in order to receive the EMG signal from the correct muscle and to provide the stimulation pulse to this muscle.

SUMMARY OF THE INVENTION

It is one object of the invention to provide an apparatus for electrical stimulation of muscle tissue in which the need for an accurate positioning of the electrode is obviated.

The electrode system described herein can be positioned with a lower degree of precision without affecting the stimulation of the muscle, since for the stimulation one or more electrode pads of the electrode array can be selected, which electrode pads are present in the area suitable for providing the stimulation signal. Accordingly, in case a part of the electrode array is positioned outside the area suitable for providing the stimulation signal, the stimulation signal can still be provided by the electrode pads which are positioned in this area.

Furthermore, since the electrode system includes both the electrode array and a sensor for measuring the activity of the muscle, the sensor will measure the activity in or nearby the area that is to be stimulated. Thus, the effect of the stimulation can be determined more accurately. Also, since the electrode system can be positioned with a lower degree of precision, the electrode system can be placed by a person without specialist knowledge about the muscle system.

Specific embodiments of the invention are set forth in the dependent claims.

Some embodiments have the further advantage that the electrode pads can be used to stimulate and to measure and thus the need for a separate sensor for the measurement is obviated.

Some embodiments have the further advantage that the apparatus can automatically determine which electrode pads have the most optimal contact with the muscle tissue.

Some embodiments have the further advantage that a user of the apparatus can perceive the effect of the stimulation on his or her muscles.

Some embodiments have the further advantage that the user can understand the effect without requiring specialist knowledge.

Some embodiments have the further advantage that the muscle tissue can be measured and stimulated in a non-invasive manner by positioning the electrode system on the skin. Another advantage is that the electrode system can be placed on various body parts due to the carrier of the flexible material.

Some embodiments have the further advantage that in operation the measurements and stimulation are automatically performed in the correct order.

Some embodiments have the further advantage that the effect of the stimulation on the muscle tissue can be determined automatically.

Some embodiments have the further advantage that the user knows which action, e.g. flexing of body parts, to perform at a given moment without requiring knowledge or supervision by a medical expert.

Some embodiments have the further advantage that electrode pads which are not positioned correctly can be found automatically.

Some embodiments have the further advantage that automatically a stimulation suitable for the specific muscle tissue, is performed.

These and other aspects of the invention will be apparent from and elucidated with reference to the embodiments described hereinafter.

BRIEF DESCRIPTION OF THE DRAWINGS

Further details, aspects and embodiments of the invention will be described, by way of example only, with reference to the drawings.

DESCRIPTION OF PREFERRED EMBODIMENTS

Figure 1:
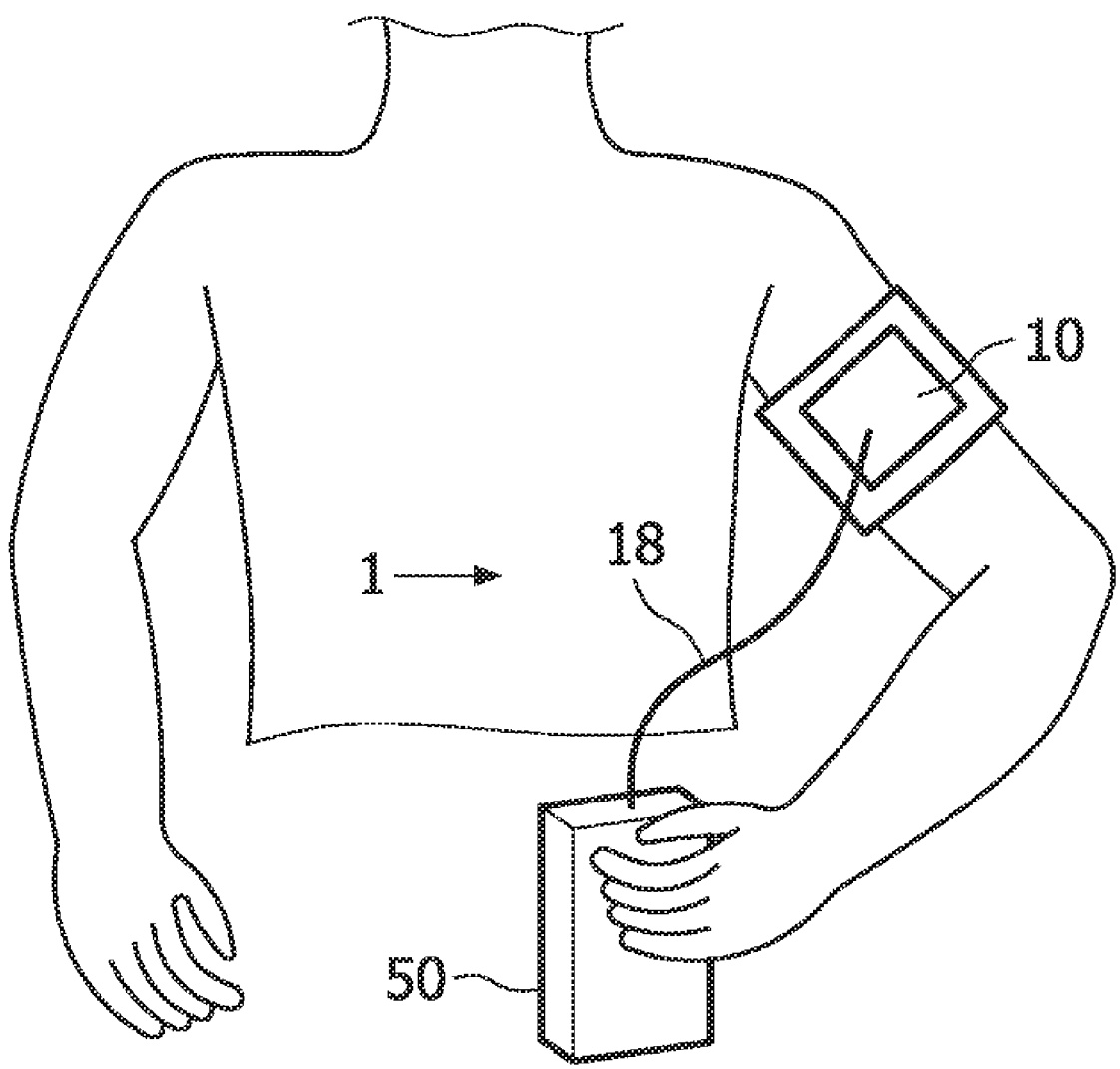
FIG. 1 shows a schematic representation of an example of an embodiment of an apparatus for stimulating muscle tissue placed on a human body.

The electro-stimulation apparatus 1 shown in FIG. 1 comprises an electrode system 10 which can be placed on the skin of an animal, such as a human being. In FIG. 1, the electrode system 10 is placed on a skin portion of the upper-arm. However, the electrode system 10 may be placed on another part of the body and may have a shape adapted to the shape of the specific body part. For example in case the electrode system 10 is to be placed on the spinal area of the body, the electrode system 10 may have an elongated shape.

As shown in FIG. 1, the apparatus 1 further includes an operation unit 50 which is connected to the electrode array 10 via a connection 18. In the example of FIG. 1, the connection 18 is a wire connection. However the connection 18 may also be a wireless connection. The operation unit 50 can receive signals generated by the electrode system 10 and control the operation of the electrode system 10, as is explained below in more detail. The operation unit 50 includes, as shown in FIG.

5, housing 54. In the inside of the housing 54, a control unit 53 is provided which is connected to the electrode system 10 via the connection 18 and to a user interface.

The user interface includes a display 51 which is placed in a window 55 of the housing 54 and control buttons 52 placed on the outside of the housing. The display 51 forms an output interface via which information can be provided to a user of the apparatus 1. At the display 51, for example, information can be outputted by the control unit 53 in a for humans perceptible form, for instance about the operation of the apparatus 1 or instructions to the user. In the example of FIG. 1, the data is outputted visually, however the data may alternatively or additionally be outputted as audio or any other suitable manner.

The control buttons 52 form an input interface. Via the control buttons 52, the user can provide input to the control unit 53, such as for example desired settings for the operation performed by the apparatus or information about an action performed by the user. For example, the user may via the control buttons 52 inform the control unit 53 that he or she has flexed a muscle or input a desired value for the duration of a period the muscle is stimulated.

Figure 2:
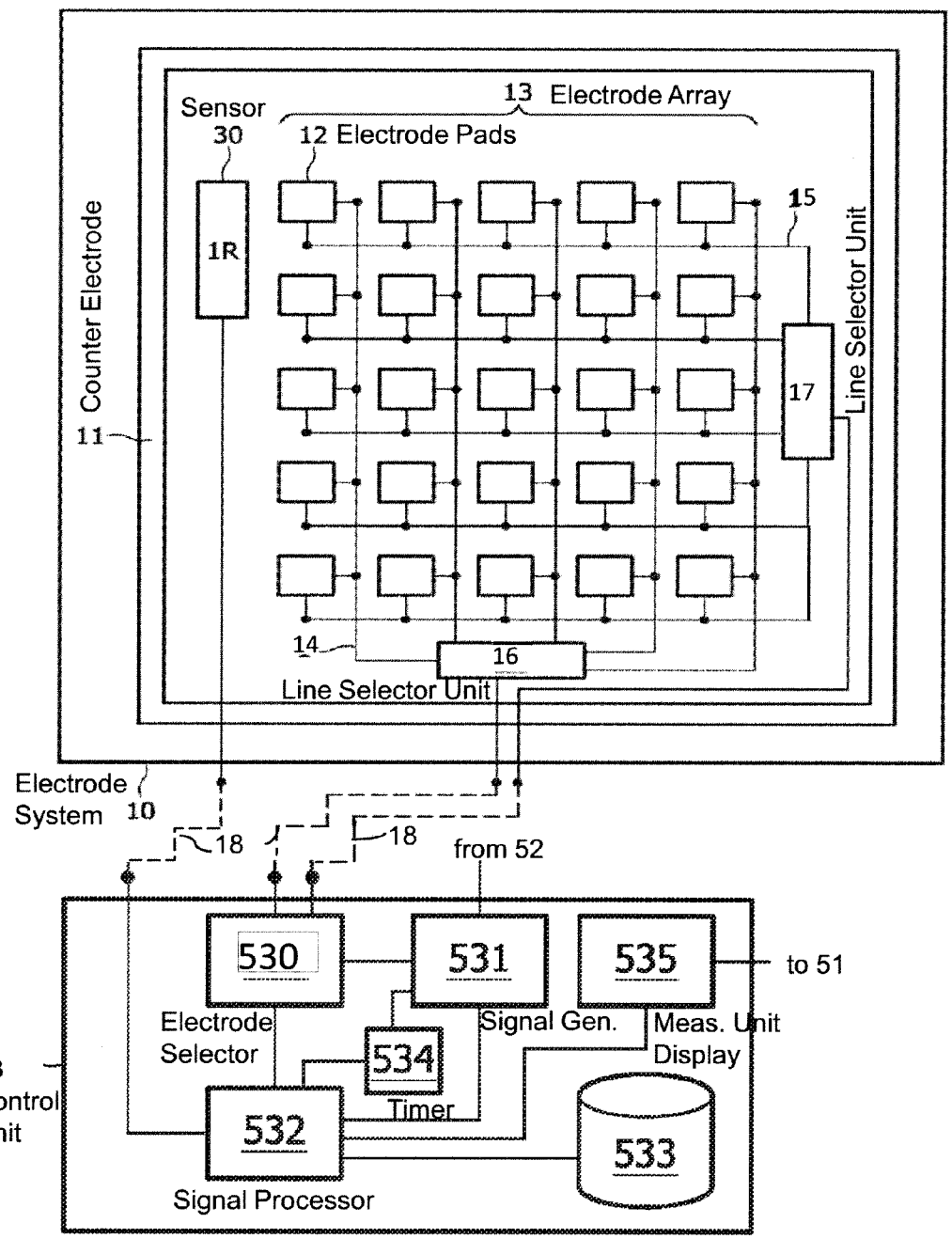
FIG. 2 shows a schematic representation of a first example of an embodiment of an electrode system connected to an example of a control unit.
Figure 4:
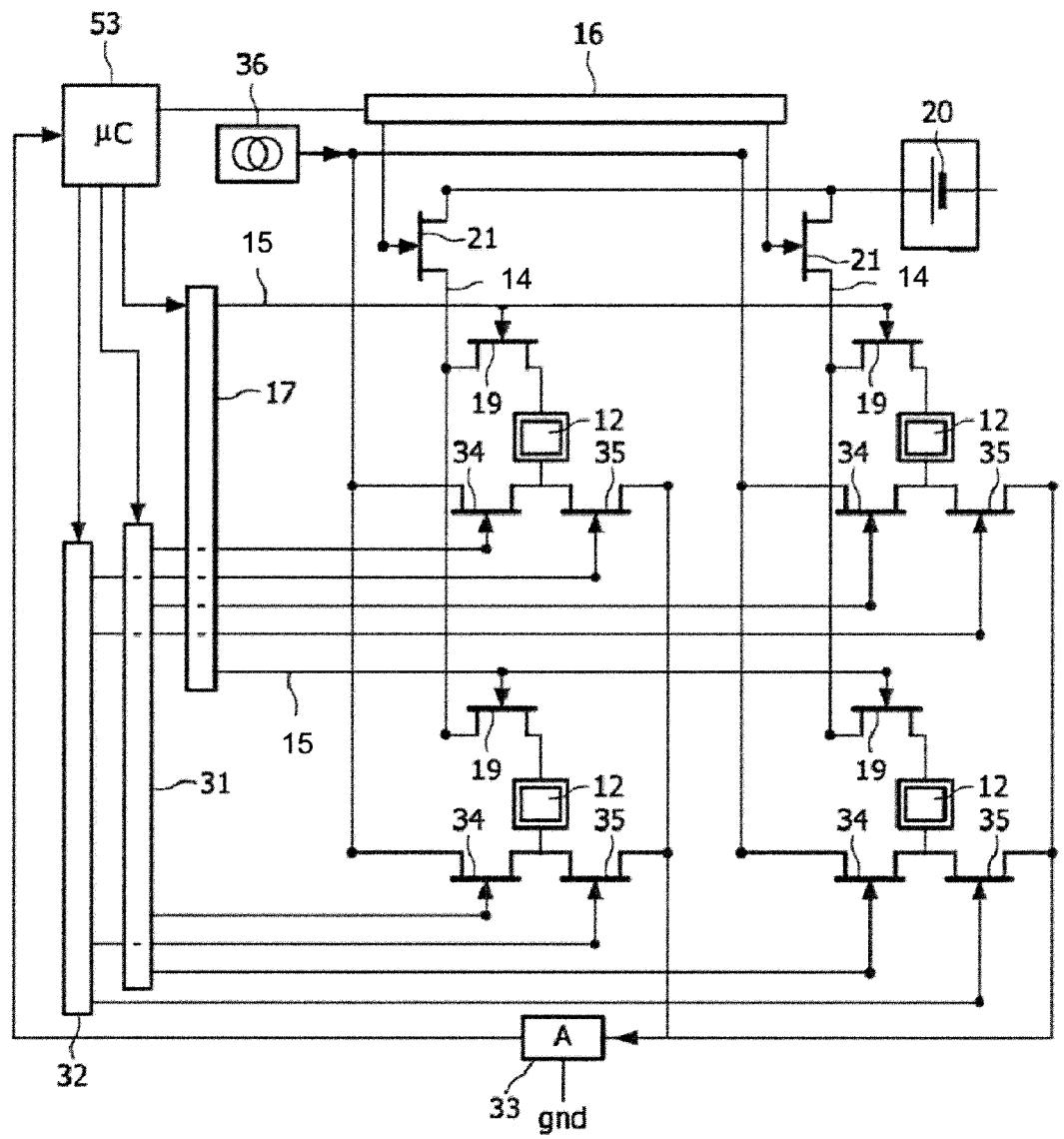
FIG. 4 shows a schematic representation of a second example of an embodiment of an electrode system.

The electrode system 10 includes, as shown in FIG. 2, an electrode array 13 with a plurality of electrode pads 12 and a counter electrode 11. The counter electrode 11 acts as ground. The electrode pads 12 in the electrode array 13 shown in FIG. 2 are positioned along straight lines, forming a rectangular matrix arrangement. In the example of FIG. 2, the matrix is a 5 by 5 matrix, however the matrix may have other dimensions, for example smaller and, as shown in FIG. 4, be a 2×2 matrix or have larger dimensions. Furthermore, the matrix may, as shown in the examples of FIGS. 2 and 4, be square or have a number of columns different from the number of rows. Furthermore, the electrode pads 12 may also be positioned in a non-rectangular arrangement, such as a circular arrangement or a triangular arrangement.

In the example of FIG. 2, the counter electrode 11 has a closed loop shape and encloses the electrode array 13. However, the counter electrode 11 may have a different shape and for example follow a meandering path between the electrode pads 12.

The electrode system 10 may be placed on the skin such that most or all of the electrode pads 12 and the counter electrode 11 make electrical contact with the skin. The electrode array 13 will then be electrically in contact with muscle tissue below the skin and more in particular, will be able to receive or transmit an electrical signal to the region of the muscle below the skin area occupied by the electrode array 13. More in particular, the electrode pads 12 will be able to inject, via the skin, a current into the muscle tissue in order to stimulate the muscle tissue.

The electrode pads 12 and counter electrode 11 may be provided on a surface of a flexible, preferably resilient, carrier. This allows the electrode system 10 to adapt to the shape of the part of the body on which the electrode system 10 is placed. The carrier may be provided with electrical components connecting the electrode pads 12 and counter electrode 11, via the connection 18, to the operation unit 50. For instance in the example of FIG. 4, the electrical components connected to the electrode pads 12 may be placed on the carrier and be connected to a microprocessor μC placed in the operation unit 50 via a suitable connection 18.

The control unit 53 includes, as shown in FIG. 2, an electrode selector 530 for selecting from the electrode pads 12 in the electrode array 13 one or more stimulation electrode pads. In the example of FIG. 2, the electrode selector 530 is connected via the connection 18 to respective control inputs of line selector units 16,17. Each of the line selector units 16,17 can select one or more common line connections 14,15. The common line connections 14,15 connect a row of electrode pads 12 in the electrode array 13. In FIG. 2, the common line connections 14 connect vertical rows of electrode pads 12 to a first line selector unit 16 and common line connections 15 connect horizontal rows of electrode pads 12 to a second selector 17. By selecting suitable common line connections 14,15 one or more of the electrode pads can be selected.

A signal generator 531 is connected to the electrode selector 530. In operation, the signal generator 531 provides an electrical stimulation signal to the stimulation electrode pads. The electrical stimulation signal is transferred via the stimulation electrode pads to the surface on which the electrode system is placed, e.g. the skin. The electrode signal then penetrates via the skin into the muscle tissue, in response to which the muscles tissue contracts. Thereby, the muscle tissue is stimulated.

The values of the parameters for the stimulation, such as for example the amount of current and the duration of the stimulation period, may be determined by the signal generator 531 based on data stored in a memory of the signal generator 531. However, it is also possible that the signal generator 531 determines the parameters of the stimulation in a different manner. For instance in the example of FIG. 2, the signal generator 531 can receive via the control buttons 52 user-defined settings of the stimulation, such as duration and magnitude. Furthermore, the signal generator 531 in the example of FIG. 2 is connected to the signal processor 532 and can determine suitable settings for the stimulation based on the activity measured in a period shortly, or directly, before the stimulation. For example, the signal processor 532 may be programmed to calculate a suitable duration and magnitude of the stimulation from the measured activity, using a pre-defined mathematical relationship. The signal generator 531 may determine the setting of the parameters of the stimulation in other manners as well, and for example determine suitable settings of the parameters from a pre- and post-stimulation measurement of a series of stimulations.

In the example of FIG. 2, the electrode system 10 includes a separate sensor 30. The sensor 30 can sense a property of the muscle tissue, which property forms a measure for the activity of said muscle tissue. In this example, the sensor 30 is an infrared sensor which can receive infrared radiation from the surface on which the electrode system 10 is placed. Without being bound to any theory, it is believed that the circulation of blood is related to the activity of the muscle and that the amount of infrared radiation forms a measure for the circulation of blood in the muscle. The sensor 30 has a sensor output which is connected to a processor input of a signal processor 531 in the control unit 53. Via the sensor output, the sensor 30 can provide a sensor signal to the signal processor 532. The signal processor 532 can determine from the sensor signal a value of the measure for the activity and output the value via a processor output. The processor output may for example be connected to the display 51, in order to output the value in a for humans perceptible form.

In the example, the output of the signal processor 532 is connected to a measuring unit 535. The measuring unit 535 is connected with an output to the user-interface, i.e. in this example the display 51. The measuring unit 535 can determine a parameter of the muscle tissue based on the value determined by the signal processor 532 and output this value in a for the user perceptible form at the user-interface, e.g. as a digit on the display 51. The measuring unit 535 may for example calculate the maximum force by the muscle tissue is able to deliver, based on the value for the activity of the muscle tissue. However, the measuring unit 535 may determine other parameters of the muscle tissue, e.g. based on a predetermined relationship the measuring unit 535 may determine the response time of the muscle tissue or another parameter of interest to the user.

The control unit 53 shown in FIG. 2 further includes a timer 534 which can control the order of operation of the signal generator 531 and the signal processor 532 such that in operation a predetermined sequence of measuring and stimulating is performed. The timer 534 may for example be arranged to transmit a start signal to the signal processor 532 and/or the signal generator 531 after a certain event, for example in response to a stop signal received from the signal generator 531 and/or signal processor 532 after termination of the stimulation or measuring, respectively.

Figure 3:
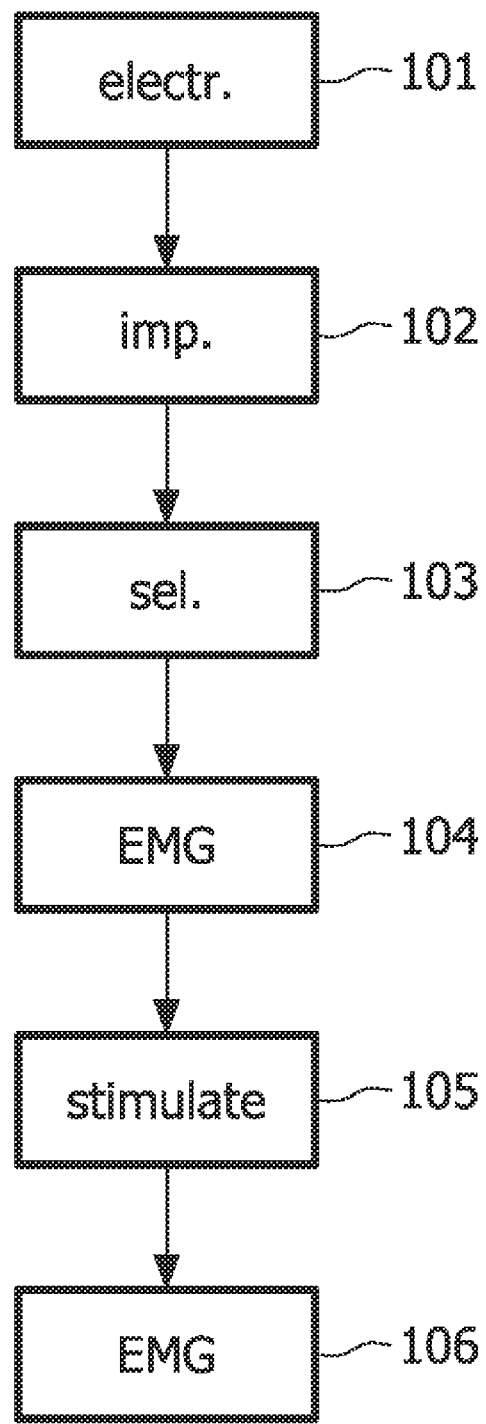
FIG. 3 shows a flow chart of an example of a method for stimulating muscle tissue.

FIG. 3 shows a flow-chart of an example of a suitable sequence. After the electrode system 10 is positioned in a first step 101 on a desired surface, for example a part of the skin that feels painful to the user, the impedance between each of the electrode pads 12 and the skin is measured in a second step 102. Based on the measured impedance, one or more stimulation electrode pads 12 are selected in a third step 103. In case the electrode pads 12 are also used to measure the activity of the muscle tissue below the skin, e.g. by measuring the electromyogram (EMG), the measuring electrode pads may also be selected based on the measured impedance.

For example, one or more electrode pads 12 with the lowest impedance may be selected. Without being bound to any theory, it is believed that the area of the skin nearby the lowest impedance electrode pad is the most suitable for measuring the activity of the muscle tissue. Furthermore, it is believed that this area is also the most suitable for stimulating the muscle tissue.

It is also possible to select, in addition to an electrode pad 12 with the lowest impedance, one or more electrode pads 12 in the vicinity of these electrode pads, e.g. the electrode pads 12 which, in the electrode array 13, are adjacent to the electrode pad 12 with the lowest impedance. Thereby, the stimulation and/or measurement is less sensitive to local artifacts while still a suitable area is used to measure and/or stimulate the muscle tissue.

The same electrode pads 12 may be selected for the measurement and the stimulation. The selected electrode pads 12 are then used to both measure the activity and stimulate the muscle tissue. This allows a reduction of the amount of electrode pads 12 and electronic circuitry to control the electrode pads 12. However, it is also possible that for measuring the activity of the muscle tissue, other electrode pads 12 are used than the electrode pads 12 used to stimulate the muscle tissue. For example, the stimulation electrode pads 12 may be selected based on spatial information about the activity of the muscle tissue. For instance, each electrode pad 12 may be used to measure the activity of the muscle tissue and the stimulation electrode pads 12 may be selected based on the area in which the muscle exhibits the lowest activity.

The measured impedance may be compared for each electrode pad 12 with a threshold value. In case the measured impedance between an electrode pad 12 and the surface, e.g. the skin, exceeds the threshold value, a warning signal may be provided to the user indicating that the electrical contact between the respective electrode pad 12 and the skin is not sufficient. In response to the warning signal, the user may move (a part) of the electrode system 10 in order to improve the electrical contact.

Prior to an electrical stimulation of the muscle tissue, a first measurement of the measure for the activity of the muscle tissue is performed in a fourth step 104. Before the fourth step 104 is initiated, the user may be instructed by the apparatus 1 to perform a certain physical activity and the muscle activity in the area on which the electrode system 10 is provided may be measured. For example, the user may be instructed by means of a suitable message on the display 51. The physical activity may for example be to move the part of the body on which the electrode system 10 is provided. Thereby, e.g. the maximum activity may be measured. The measured activity of the muscle tissue may be outputted in a perceptible form, for example at the display 51 in the example of FIG. 2. The measured activity may be outputted directly after the first measurement is performed or later.

After the first measurement, the muscle tissue is stimulated in a fifth step 105. During stimulation, an electrical signal is provided by means of the stimulation electrode pads 12. The electrical signal is such that the muscle tissue alternately contracts and relaxes. This is believed to have a therapeutic effect on the muscle tissue. More specific, this is believed to reduce the muscular stiffness and to reduce myalgia.

After stimulating the muscle tissue, a second measurement of the activity of the muscle tissue is performed in a sixth step 106. Based on the measurement, other properties of the muscle tissue may be derived, such as the maximum muscle force of another parameter which is related to the health of the muscle tissue. Thus, the effect of the stimulation on the activity of the muscle tissue can be determined. Before the sixth step 106 is initiated, the user may be instructed by the apparatus 1 to perform a certain physical activity and the muscle activity in the area on which the electrode system 10 is provided may be measured. For example, the user may be instructed by means of a suitable message on the display 51. The physical activity may for example be to move the part of the body on which the electrode system 10 is provided.

Without being bound to any theory, it is believed that the stimulation reduces the muscular stiffness and myalgia. It is further believed that stiff or myalgic muscle tissue exhibits a lower activity. Thus, by outputting the value of the activity before and after the stimulation, the effect of the stimulation on the muscle tissue can be determined.

The values for the activity determined before and after the stimulation may be outputted to the user-interface. Thus, a user can perceive the effect of the stimulation in a simple manner. Instead or in addition to the measured activity, another parameter derivable from the first and second measurement in step 104 and 106 may be outputted, such as the maximum muscle force before and after the stimulation in step 105. The maximum force of stiff or myalgic muscle tissue is lower, and accordingly the effect of the stimulation on the stiffness or myalgia can be understood without specialist knowledge in case the maximum force is presented at the user-interface.

Furthermore, the determined values may be stored in a memory 533. Thereby, the effect of the stimulation over a series of stimulations can be determined. For example, the muscle tissue may be stimulated on a daily basis for a certain period of time, e.g. 15 minutes, and the effect over a couple of days may be determined. As shown in FIG. 2, to that end, for example, a memory 533 may be connected to the signal processor 532 and the signal processor 532 may store data representing the measured values and information about the time of measurement in the memory 533.

FIG. 4 shows a second embodiment of an electrode system 10. The electrode system includes a 2 by 2 matrix arrangement of electrode pads 12. The electrode pads 12 are connected to a first selecting element 16 via common line connections 14 and to a second selecting element 17 via common line connections 15. Between each of the electrode pads 12 and the common line connections 14,15 a transistor 19 is provided which operates as a switch. The gate of each transistor 19 is connected to a common line connection 15 controlled by the second selecting element 17. The source of each transistor 19 is connected to a common line connection 14 controlled by the first selecting element 16 and the drain of each transistor 19 is connected to a respective electrode pad 12.

Connected to the selecting elements 16,17 is a microcontroller µC. The microcontroller µC is programmed to perform the functions of the control unit 53. The microcontroller µC can, inter alia, control the selection elements 16,17 and transmit control data to the selection elements 16,17 in response to which a common line connection 14,15 is selected by the selection elements 16,17 according to the control data.

The first selecting element 16 can select, under the control of the microcontroller µC, one or more common line connections 14 and provide electrical power to the transistors 19 connected to the selected common line connections 14. The electrode system 10 includes an electrical power source 20 connected to the common line connections 14 via switches 21. The first selecting element 16 can control the state of the switches 21 to be either open or closed. In the open state, the switch 21 allows a current to flow from the power source 20 to the common line connection 14, whereas in the closed state the switch 21 inhibits the current to flow. In the example of FIG. 4, the switches 21 are implemented as switching field effect transistors connected with their gate to the first selecting element 16. The sources of the switching transistors are connected to the power source 20, and the drains to the common line connection 14. By controlling the gate to be open, a current is allowed to flow between source and drain of the switching transistor, whereas the current is inhibited in case the gate is closed. Thus, the first selecting element 16 can control through which specific common line connection 14 the power source provides electrical power and accordingly select the electrode pads 12 connected to this common line connection 14.

The second selecting element 17 can provide a switch signal to selected ones of the common line connections 15. The switch signal causes the switching transistors 19 to be either in a conducting state in which a current flows between source and drain of the switching transistors 19 or in a non-conducting in which substantially no current flows between the source and the drain of the switching transistors 19. Thus, by providing a suitable switch signal to the selected common line connections 15, the switching transistor 19 connected to the selected common line connections can be set in the conducting state in which a current is provided to the electrode pads 12 whereas the switching transistors 19 connected to the selected common line connections 15 in the non-conducting state do not provide a current to the respective electrode pad 12.

The electrode pads 12 are each further connected to first and second measurement transistors 34,35. The measurement transistors 34,35 are pair-wise connected to an electrode pad 12 via a node between the transistors 34,35. The source of the first measurement electrodes 34 is connected to a current source 36 which provides a predetermined amount of current. The gate of the first measurement transistor 34 is connected to a measuring mode selecting unit 31. The measuring mode selecting unit 31 can select one or more first measurement transistors 34. In the example of FIG. 4, the measuring mode selecting unit 31 is connected to the microcontroller µC. The microcontroller µC can control the operation of the measuring mode selecting unit 31. The measuring mode selecting unit 31 can open or close the gate of the first measurement transistor 34. In case the gate is open a current between source and drain is allowed. In case the gate is closed a current between source and drain is inhibited. The drains of the first measurement electrodes 34 are connected to the electrode pad 12 and to the second measurement transistor 35. By opening the gate of a first measurement transistor 34, a current is provided to a selected electrode pad 12 and to a second measurement transistor 35 whereas in case the gate of a first measurement transistor 34 is closed, the selected electrode pad 12 and the second measurement transistor 35 may be regarded as electrically isolated from the current source 36.

The source of each of the second measurement transistors 35 is connected to an electrode pad 12. The drain is connected to ground gnd (e.g. the counter electrode 11) via an ampere or current meter 33. The gate of each of the second measurement transistors 35 is connected to a measuring electrode selecting unit 32. The measuring electrode selecting unit 32 is connected with a control input to the microcontroller µC. The measuring electrode selecting unit 32 can, controlled by the microcontroller µC, open or close the gate of one or more selected second measurement transistors 35. In case a voltage difference exits between the electrode pad 12 and ground, for example due to the activity of the muscle tissue in the region of the electrode pad 12, a current will flow through the second measurement transistor 35 and the current meter 33. By opening or closing the gate of the respective second measurement transistor 35, the current between the electrode pad 12 and ground is either allowed or inhibited. Thus, in case no current is provided via a first measurement transistor 34, by selecting a respective one of the second measurement transistors 35 to be open and the other second measurement transistors 35 to be closed, the voltage at the electrode pad 12 connected to the open second measurement transistor 35 can be determined. Hence, the electrical activity of the muscle tissue in contact with the selected electrode pad 12 can be measured.

In case the respective first measurement transistor 34 is conducting, a first part of the provided current will flow to the electrode pad 12 and a second part to the current meter 33, via the second measurement transistor 35. The ratio of the first part and second part is dependent on, inter alia the impedance between the electrode pad 12 and the skin. Thus, this impedance can be determined by comparing the current measured by the current meter 33 with the predetermined current provided by the current source 36. The first measurement transistor 34 thus acts as a selector for the measuring mode, in this example an impedance measuring mode and a muscle tissue activity measuring mode, whereas the second measurement transistor 35 is used to select the specific electrode pad 12 that is measured. In case, for example, the electrode pad 12 does not make a sufficient contact, the impedance will be very high and (almost) no current will flow through the electrode pad 12. Thus, substantially the same amount of current will flow through the current meter 33 as is provided by the current source 36. Accordingly, by comparing the current measured by the current meter 33 with a suitable threshold value, an impedance which is too high can be determined.

In the example of FIG. 4, the current meter 36 is connected to the microcontroller µC. The current meter 36 can transmit the value of the measured amount of current to the microcontroller µC. The microcontroller µC can determine from the value the impedance between the electrode pads 12 and the skin and can select, based on the impedance, suitable electrode pads. The microcontroller µC can for example control the measuring electrode selecting unit 32 such that impedance between each individual electrode pad 12 and the skin is measured separately via the current meter 33. The microcontroller µC may then select one or more electrode pad(s) via the measuring mode selecting unit 31 and the measuring electrode selecting unit 32 and measure the activity of the muscle tissue and stimulate the muscle tissue at the location of the selected electrode pads 12 via the line selector units 16 and 17.

Figure 6:
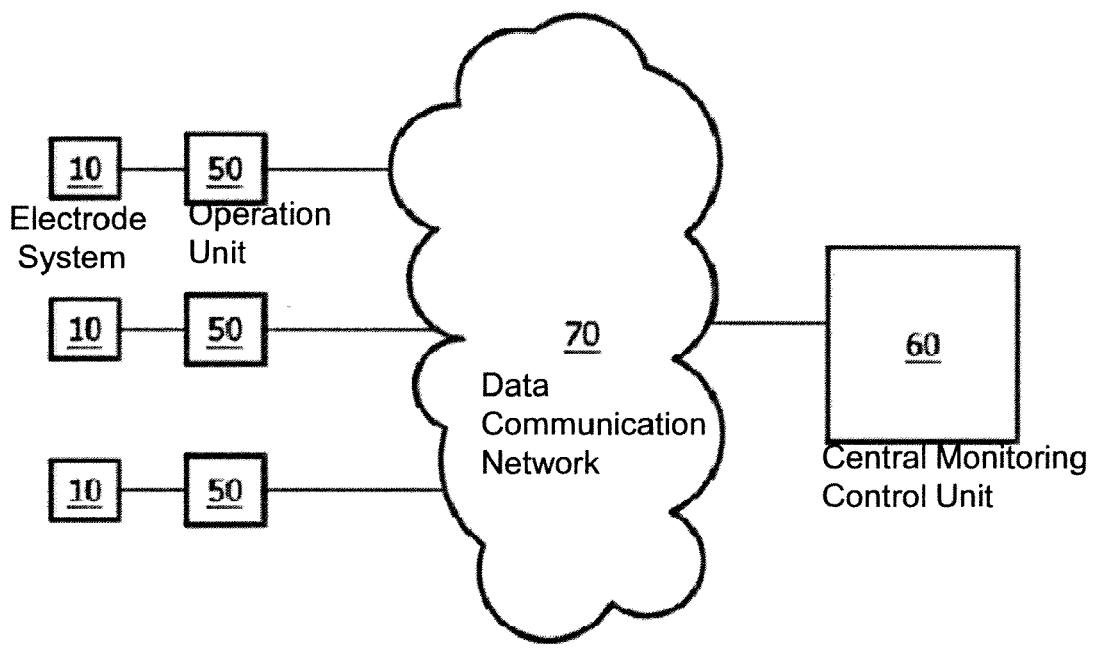
FIG. 6 shows a schematic representation of an example of an embodiment of a remote monitoring system according to the invention.

The electrode system 10 may be used to monitor and/or control a treatment of the muscles at a remote location. For example, as shown in FIG. 6, the electrode system may be used in a remote monitoring and control system. The example of FIG. 6 includes a plurality of electrode systems 10 is connected to a central monitoring and control unit 60. In the example of FIG. 6, the central monitoring and control unit 60 is connected to a data communication network 70. The electrode systems 10 are connected to the data communication network 70 via operation units 50.

In the example of FIG. 6, the operation units 50 can transmit via the data communication network 70 measurement data representing the measured activity of the muscle tissue to the central monitoring and control unit 60. At the central monitoring and control unit 60, a medical expert such as a physician or a physiotherapist, can perceive the measurement data and determine a suitable treatment of the muscle tissue. The expert may subsequently input suitable settings for the stimulation corresponding to the treatment to the central monitoring and control unit 60. The central monitoring and control unit 60 can transmit the control data to the operation unit 50 via the data communication network 70. In response to the control data, the operation unit 50 controls the operation of the electrode system 10.

Since the electrode system 10 can be placed on the skin without specialist medical knowledge, the electrode system 10 can be placed at a location remote from the position of the central monitoring unit 60. Accordingly, in the example of FIG. 6, a user of the electrode system 10 does not need to visit a hospital or a practice of the medical expert, whereas via the central monitoring and control unit 60, the medical expert can still apply his expertise by monitoring and controlling the treatment.

Figure 5:
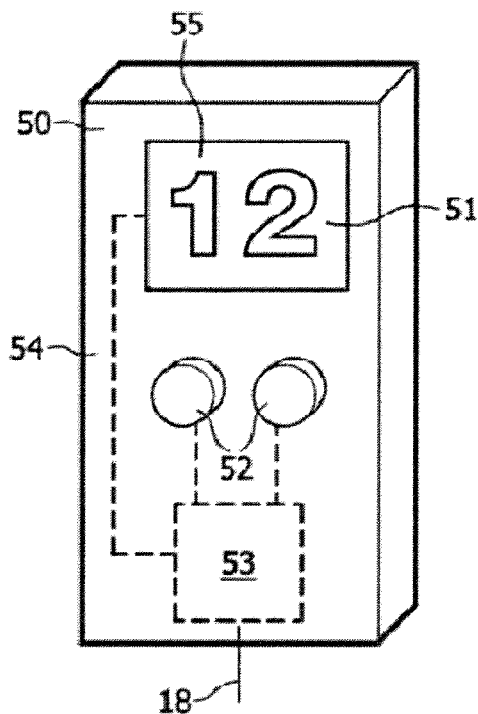
FIG. 5 shows a schematic representation of an example of an embodiment of an operation device

In the example of FIG. 6, the operation units 50 may for example be implemented as shown in FIG. 5 and further include a network module which allows communication with the network 70, for instance via a wired connection or a wireless connection. The network may for example connected to the output of the measuring unit 535 and to the input of the signal generator 531 to transmit the measurement data and to receive the control data.

In the foregoing specification, the invention has been described with reference to specific examples of embodiments of the invention. It will, however, be evident that various modifications and changes may be made therein without departing from the broader spirit and scope of the invention as set forth in the appended claims. For example, the transistors shown in the examples may be replaced with other types of switches. Furthermore, the control unit 53 and the electrode system 10 may be integrated. Also, the invention is not limited to physical devices or units implemented in non-programmable hardware but can also be applied in programmable devices or units able to perform the desired device functions by operating in accordance with suitable program code. Furthermore, the devices may be physically distributed over a number of apparatuses, while functionally operating as a single device. For example, the electrode selector 530 may be implemented as a number of device cooperating to select electrode pads 12. Also, devices functionally forming separate devices may be integrated in a single physical device. For example, the electrode selector 530, the signal generator 531, the signal processor 532, the memory 533, the timer 534 may be implemented in a suitably programmed microcontroller or in a single integrated circuit. However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the words 'a' and 'an' shall not be construed as limited to 'only one', but instead are used to mean 'at least one', and do not exclude a plurality. The mere fact that certain measures are recited in mutually different claims does not indicate that a combination of these measures cannot be used to advantage.

The invention claimed is:

1. An apparatus for electrical stimulation of muscle tissue, comprising:
    an electrode system comprising:
    a flexible carrier of a flexible material which is configured to be placed against skin nearby muscle tissue to be stimulated;
    an electrode array arranged on the flexible carrier comprising a plurality of electrode pads positioned in rows and columns wherein the electrode pads are positioned at a surface of the flexible carrier, wherein the electrode pads are in electrical communication with said muscle tissue when the flexible carrier is placed against the skin nearby the muscle tissue;
    a row selector unit and a column selector unit positioned on the flexible carrier which select individual electrode pads based on their row and column location;
    an electrode selector which communicates to the row selector unit and the column selector unit the row and column locations of the individual electrode pads to be selected;
    individual electrode pads in the electrode array being selected and used to measure muscle activity of the muscle tissue based on an electrical signal received by the selected electrode pad; and
    a signal generator connected to said electrode array which signal generator generates an electrical signal of selected current and duration to said at least one selected electrode pad.

2. The apparatus according to claim 1, further comprising:
    a measuring unit which is connected to the selected electrode pads used to measure muscle activity of the muscle tissue and input the electrical signal from the selected electrode pads and output a value of said measure for the electrical activity of said muscle tissue or of a property derived from said measure in a perceptible form.

3. The apparatus according to claim 2, further comprising:
    a signal processor which inputs the measure of muscle activity from the measuring unit, calculates an amount of current and a duration to be applied during a stimulation period, and outputs the calculated amount of current and the calculated duration to the signal generator.

4. The apparatus according to claim 3, further comprising:
    a sequence control circuit which controls the operation of the signal processor and the signal generator such that in operation a predetermined sequence of measuring and stimulating is performed.

5. The apparatus according to claim 4, wherein the predetermined sequence includes a first measuring of the measure for the activity of the muscle tissue, a stimulation of the muscle tissue after the first measuring, and a second measuring of the measure for the activity of the muscle tissue after the stimulation of the muscle tissue.

6. The apparatus according to claim 1, further comprising a user interface which outputs a signal to a human being, the signal representing instructions to perform a predetermined action with a part of the body of the human being.

7. The apparatus according to claim 1, further comprising:
an electronic circuit which measures an impedance between at least one of the selected electrode pads and a surface on which the electrode array is positioned.

8. An apparatus according to claim 7, further comprising:
a control unit connected to the electronic circuit for measuring the impedance, comparing the measured impedance with a threshold and outputting a warning signal in response to the measured impedance exceeding the threshold.

9. An electrode system, comprising:
an electrode array comprising a plurality of electrode pads, wherein the electrode array is configured to be placed on skin of a person in electrical contact with muscle tissue, said electrode array being connected to an electrode selector which selects from said plurality of electrode pads at least one stimulating electrode pad and provides an electrical stimulation signal to said at least one stimulation electrode pad; and
a sensor for sensing a property of said muscle tissue, which property forms a measure for the activity of said muscle tissue, the sensor comprising a measuring circuit which measures an impedance between at least two of the electrode pads and a surface of the skin on which the electrode array is placed.

10. An apparatus for electrical stimulation of muscle tissue comprising:
an array of electrodes configured to be positioned on skin of a body surface covering the muscle tissue to be stimulated, the array of electrodes being arranged in a plurality of rows and columns:
a row selector unit connected to the array which selects one or more of the electrode rows;
a column selector unit connected to the array which selects one or more of the electrode columns;
one or more sensors which measure an activity of the muscle tissue, the measured activity being based on an impedance between one or more electrodes and the body surface on which the electrode array is positioned;
an electrode selector connected to the row selector unit and the column selector unit to select a subset of the electrodes of the array based on the measured activity; and
a signal generator that provides an electrical signal to the selected subset of the electrodes.

11. The apparatus of claim 10, wherein the electrode selector is connected wirelessly to the row selector unit and the column selector unit.

12. An apparatus for electrical stimulation of muscle tissue, comprising:
an electrode system comprising:
a flexible carrier of a flexible material which is configured to be placed against skin nearby muscle tissue to be stimulated;
an electrode array arranged on the flexible carrier comprising a plurality of electrode pads positioned in rows and columns wherein the electrode pads are positioned at a surface of the flexible carrier, wherein the electrode pads are in electrical communication with said muscle tissue when the flexible carrier is placed against the skin nearby the muscle tissue;
a row selector unit and a column selector unit positioned on the flexible carrier which select individual electrode pads based on their row and column location;
an electrode selector which communicates to the row selector unit and the column selector unit the row and column locations of the individual electrode pads to be selected;
a signal generator connected to said electrode array which signal generator generates an electrical signal of selected current and duration to said at least one selected electrode pad; and
an alarm connected to the electrode system which compares a measured impedance with a threshold and outputs a warning signal in response to the measured impedance exceeding the threshold.

13. An apparatus as claimed in claim 12, further comprising:
a display device which outputs to a user of the apparatus at least one of instruction and information about the operation of the apparatus; and
an input device by which the user inputs information or instructions to be used by the apparatus.

14. The apparatus of claim 13, further including:
a data network communication device connected to electrode selector which remotely monitors the operation of the apparatus.

15. The apparatus according to claim 12, wherein the electrode system includes a sensor which senses a property of the muscle tissue.

16. The apparatus of claim 12, wherein the electrode selector wirelessly communicates with row and column selector units.

* * * * *